United States Patent
Felder et al.

(10) Patent No.: US 8,252,819 B2
(45) Date of Patent: Aug. 28, 2012

(54) LOW-MELTING BIOCIDAL FORMULATION

(75) Inventors: Patrick Thomas Felder, Grabs (CH); Gerhard Tiedtke, Gams (CH)

(73) Assignee: Rohm and Haas Company, Philadelphia, PA (US)

( * ) Notice: Subject to any disclaimer, the term of this patent is extended or adjusted under 35 U.S.C. 154(b) by 442 days.

(21) Appl. No.: 12/384,872

(22) Filed: Apr. 8, 2009

(65) Prior Publication Data
US 2009/0258916 A1 Oct. 15, 2009

Related U.S. Application Data

(60) Provisional application No. 61/123,973, filed on Apr. 11, 2008.

(51) Int. Cl.
- *A01N 43/40* (2006.01)
- *A01N 43/80* (2006.01)
- *A61K 31/44* (2006.01)
- *A61K 31/425* (2006.01)

(52) U.S. Cl. .................. 514/357; 514/372; 514/373

(58) Field of Classification Search .................. 514/357, 514/372
See application file for complete search history.

(56) References Cited

U.S. PATENT DOCUMENTS

| | | | |
|---|---|---|---|
| 3,097,131 A | | 7/1963 | Ryuzo et al. |
| 4,309,564 A | | 1/1982 | Loncrini et al. |
| 4,357,258 A | | 11/1982 | Haag et al. |
| 4,496,576 A | | 1/1985 | Loncrini et al. |
| 5,468,759 A | | 11/1995 | Hsu |
| 5,591,760 A | | 1/1997 | Hsu |
| 6,294,186 B1 | * | 9/2001 | Beerse et al. ............. 424/405 |
| 6,310,013 B1 | * | 10/2001 | Lokkesmoe et al. ....... 508/502 |
| 2004/0198713 A1 | * | 10/2004 | Heer et al. ................ 514/184 |
| 2007/0258915 A1 | * | 11/2007 | Kielbania ................. 424/53 |
| 2007/0292465 A1 | | 12/2007 | Parkin et al. |

FOREIGN PATENT DOCUMENTS
| | | |
|---|---|---|
| EP | 1382248 | 1/2004 |
| EP | 1421852 | 5/2004 |

* cited by examiner

*Primary Examiner* — Sreeni Padmanabhan
*Assistant Examiner* — Layla Soroush
(74) *Attorney, Agent, or Firm* — Kenneth Crimaldi

(57) ABSTRACT

A low-melting biocidal composition comprising 4,5-dichloro-2-octyl-3(2H)-isothiazolone, 3-iodopropargyl-N-butyl carbamate and at least one $C_1$-$C_4$ alkyl 4-hydroxybenzoate. The composition is stable with regard to agglomeration and crystallization at room temperature.

10 Claims, No Drawings

US 8,252,819 B2

LOW-MELTING BIOCIDAL FORMULATION

This application claims the benefit of priority under 35 U.S.C. §119(e) of U.S. Provisional Patent Application No. 61/123,973 filed on Apr. 11, 2008.

This invention relates generally to a stable low-melting biocidal composition, and to a stable aqueous dispersion of a low-melting, solid biocide.

Biocidal active ingredients used for protection of coatings, such as exterior paints need to have low water solubility to prevent rapid leaching upon repeated exposure to rain. Adding such active ingredients into the matrix to be protected therefore can either be done by dosing the powder directly, or by preparing concentrated solutions in organic solvents or flowable dispersions. Handling of pure powders of such biologically active substances in technical manufacturing environments involves significant risk to employees of exposure to toxic dust. Such powders also have a wide variation in particle size which can limit the overall microbiological efficacy.

Solutions of the active ingredient in organic solvents are typically limited in concentration, and thus introduce considerable amounts of organic solvent (VOC) into the environment, and also are rather expensive. Flowable aqueous dispersions can be more concentrated than solutions, have less VOC and secure even distribution and uniform microbiological efficacy due to reduced particle size. They also minimize the risk of workforce exposure to the active ingredient and are commonly used in the industry. For example, U.S. Pub. No. 2007/0292465 discloses low-melting mixtures of phenolic biocides which can be used to make aqueous dispersions. However, this reference does not teach stable low-melting mixtures containing DCOIT and IPBC. The problem addressed by this invention is to produce a low-melting mixture comprising DCOIT and IPBC.

STATEMENT OF THE INVENTION

This invention is directed to a biocidal composition comprising a mixture of from 50% to 70% 4,5-dichloro-2-octyl-3(2H)-isothiazolone; from 20% to 30% 3-iodopropargyl-N-butyl carbamate; and from 5% to 30% of at least one $C_1$-$C_4$ alkyl 4-hydroxybenzoate.

In some embodiments of the invention, the composition comprises from 10% to 18% 4,5-dichloro-2-octyl-3(2H)-isothiazolone, from 4.5% to 9% 3-iodopropargyl-N-butyl carbamate, from 2% to 8% of at least one $C_1$-$C_4$ alkyl 4-hydroxybenzoate, from 50% to 72% water, and from 10% to 20% of a combination of surfactants, fillers and thickeners.

DETAILED DESCRIPTION OF THE INVENTION

All temperatures are in °C., unless specified otherwise. All ratios are by weight, and all percentages are by weight, unless specified otherwise. An "inorganic material" is a material that is substantially free of carbon, with the exception of carbon in the form of carbonates. An "inorganic filler" is an inorganic material having a particle size less than 100 microns, and capable of remaining suspended in an aqueous dispersion. A "thickener" is a material which alters the rheological properties of an aqueous system to increase low-shear viscosity without greatly increasing viscosity at moderate shear rates, i.e., "pourability."

The composition of this invention comprises a mixture of 4,5-dichloro-2-octyl-3(2H)-isothiazolone ("DCOIT"), 3-iodoprop argyl-N-butyl carbamate ("IPBC"), and at least one $C_1$-$C_4$ alkyl 4-hydroxybenzoate. In some embodiments of the invention the at least one $C_1$-$C_4$ alkyl 4-hydroxybenzoate is at least one of methyl 4-hydroxybenzoate, ethyl 4-hydroxybenzoate and propyl 4-hydroxybenzoate; alternatively at least one of methyl 4-hydroxybenzoate and propyl 4-hydroxybenzoate; alternatively methyl 4-hydroxybenzoate, ethyl 4-hydroxybenzoate or propyl 4-hydroxybenzoate; alternatively methyl 4-hydroxybenzoate or propyl 4-hydroxybenzoate; alternatively methyl 4-hydroxybenzoate. In some embodiments of the invention the composition comprises a mixture of from 52% to 68% DCOIT, from 20% to 28% IPBC and from 10% to 25% of at least one of methyl, ethyl and propyl 4-hydroxybenzoate; alternatively from 52% to 65% DCOIT, from 20% to 26% IPBC and from 15% to 25% of at least one of methyl, ethyl and propyl 4-hydroxybenzoate; alternatively from 53% to 63% DCOIT, from 21% to 25% IPBC and from 16% to 23% of at least one of methyl, ethyl and propyl 4-hydroxybenzoate. The composition may contain additional ingredients; the percentages provided for the mixture are relative amounts of the three components, exclusive of the other ingredients.

In some embodiments of the invention, the composition further comprises at least one surfactant. In some embodiments of the invention, the composition further comprises water, at least one surfactant, at least one inorganic filler, and at least one thickener. Preferably, a mixture of 4,5-dichloro-2-octyl-3(2H)-isothiazolone, 3-iodopropargyl-N-butyl carbamate and at least one of methyl 4-hydroxybenzoate, ethyl 4-hydroxybenzoate and propyl 4-hydroxybenzoate comprises from 15% to 35% of the composition; water comprises from 50% to 75% of the composition; and a combination of surfactants, fillers and thickeners comprises from 10% to 20% of the composition. Other ingredients also may be present in small amounts, including copper salts. In some embodiments of the invention, the composition comprises from 10% to 18% 4,5-dichloro-2-octyl-3(2H)-isothiazolone, from 4.5% to 9% 3-iodopropargyl-N-butyl carbamate, from 2% to 8% of at least one $C_1$-$C_4$ alkyl 4-hydroxybenzoate, from 50% to 72% water, and from 10% to 20% of a combination of surfactants, fillers and thickeners; alternatively, from 11% to 15% DCOIT, from 5.5% to 7.5% IPBC, from 3.5% to 6% of at least one $C_1$-$C_4$ alkyl 4-hydroxybenzoate, from 55% to 65% water, and from 12% to 18% of a combination of surfactants, fillers and thickeners.

In some embodiments of the invention, the composition contains at least one copper salt. Suitable copper salts include, for example, copper dodecylbenzenesulfonate and copper EDTA complexes, including, e.g., $Na_2CuEDTA$ and $(NH_4)_2CuEDTA$. Preferably, the composition contains from 3% to 10% (of the weight of DCOIT) of at least one copper salt, more preferably from 5% to 8% (of the weight of DCOIT). In a composition comprising DCOIT, IPBC, one of the alkyl 4-hydroxybenzoates, water, surfactants, fillers, thickeners, and copper salts, preferably the amount of copper salt(s) is from 0.3% to 1.8%, more preferably from 0.5% to 1.4% (percentages based on entire composition).

Preferably, the composition contains from 50% to 100% (of the weight of DCOIT) of at least one inorganic filler, more preferably from 60% to 90% (of the weight of DCOIT). In a composition comprising DCOIT, IPBC, one of the alkyl 4-hydroxybenzoates, water, surfactants, fillers and thickeners, preferably the amount of inorganic filler(s) is from 6.5% to 13.5%, more preferably from 8% to 12% (percentages based on entire composition). Preferred inorganic fillers include, for example, calcium carbonate, silica, celite, talc, titanium dioxide, and clay, including kaolin.

Preferably, the composition contains from 7% to 37% (of the weight of DCOIT) of at least one surfactant, more preferably from 11% to 30% (of the weight of DCOIT). In a composition comprising DCOIT, IPBC, one of the alkyl 4-hydroxybenzoates, water, surfactants, fillers, and thickeners, preferably at least 1% of at least one surfactant is present in the composition, more preferably at least 1.5%, more preferably at least 2%. Preferably, the amount of surfactant(s) is no more than 6%, more preferably no more than 5%, and most preferably no more than 4.5%. Preferred surfactants include, for example, non-ionic surfactants, including 2,4,7,9-tetramethyl-5-decyne-4,7-diol; $C_9$-$C_{11}$ alcohols ethoxylated with 2-10 moles of ethylene oxide; and naphthalenesulfonic acid/formaldehyde polymers; and dodecylbenzenesulfonate metal salts. $C_9$-$C_{11}$ branched alcohols ethoxylated with 2-10 moles of ethylene oxide are especially preferred Preferably, the composition contains from 3% to 9% (of the weight of DCOIT) of at least one thickener, more preferably from 4% to 7% (of the weight of DCOIT). Suitable thickeners include, for example, xanthan gum, silicic acid salts, acrylic acid polymers and copolymers, and colloidal metal silicates. In a composition comprising DCOIT, IPBC, one of the alkyl 4-hydroxybenzoates, water, surfactants, fillers and thickeners, preferably the amount of thickener(s) is from 0.4% to 1.2%, more preferably from 0.5% to 1%.

In some embodiments of the invention, the composition comprises from 10% to 18% DCOIT; from 4.5% to 9% IPBC; from 2% to 8% of at least one of methyl 4-hydroxybenzoate, ethyl 4-hydroxybenzoate and propyl 4-hydroxybenzoate; from 50% to 72% water; from 6.5% to 13.5% of at least one inorganic filler; from 0.4% to 1.2% of at least one thickener; from 0.3% to 1.8% of at least one copper salt; and from 1% to 5% of at least one surfactant; alternatively from 11% to 15% DCOIT; from 5.5% to 7.5% IPBC; from 3.5% to 6% of at least one of methyl 4-hydroxybenzoate, ethyl 4-hydroxybenzoate and propyl 4-hydroxybenzoate; from 55% to 65% water; from 8% to 12% of at least one inorganic filler; from 0.5% to 1% of at least one thickener; from 0.5% to 1.4% of at least one copper salt; and from 1.5% to 4.5% of at least one surfactant.

In some embodiments of this invention, the composition is produced by adding surfactant(s) to water, then adding alkyl 4-hydroxybenzoate(s) and heating, preferably from 40° C. to 60° C., then adding molten DCOIT. This mixture typically is cooled, then the remaining ingredients are added. Preferably, the mixture is ground to a particle size less than 70 microns, preferably less than 50 microns, preferably at a temperature no greater than 30° C., alternatively no greater than 25° C. Particle size is determined either optically, with a scanning electron microscope, or using commercial particle size analyzers, e.g., those using laser light scattering to determine particle size. Typically, smaller particles provide greater stability to the dispersion. Preferably at least 95% of the particles are in the range from 10 μ to 50 μ, more preferably from 15μ to 40μ. Preferably, the dispersion is stable with regard to crystallization of DCOIT and/or IPBC, as well as being stable with regard to agglomeration of the particles.

The ingredients of the aqueous dispersion are agitated with any mixing equipment capable of producing a stable dispersion, for example, vacuum mixers, rotor/stator homogenizers, in-line emulsifiers, static mixers, piston homogenizers, ultrasonic homogenizers, high-speed jets or nozzles, and ball mills.

EXAMPLES

Example 1

Three-Component Mixtures Containing DCOIT & IPBC

A mixture of DCOIT:IPBC, 2:1, was combined with a third component to assess the effect of a third component on the melting point. The DCOIT/IPBC mixture had a melting point of 31-36° C. The results were best for the alkyl 4-hydroxybenzoates, data for varying percentages of which are summarized in Table 1 below. Other suitable solid compounds tested and found either to be insoluble or to lower the melting point less than the alkyl 4-hydroxybenzoates included benzisothiazolone (BIT), n-butyl BIT, carbendazim, chlorothalonil, diuron, folpet, irgarol, OIT, permethrin, propiconazole, tebuconazole, terbutryn, terbutylazine, thiabendazole, and zinc omadine. A combination of 87% 2:1 DCOIT:IPBC and two surfactants: 6.5% branched $C_{11}$ alcohol, 7 units ethylene oxide and 6.5% branched $C_9$-$C_{11}$ alcohol, 2.5 units ethylene oxide, melted at 32° C.

TABLE 1

Melting points (° C.) with methyl, ethyl and propyl 4-hydroxybenzoate as $3^{rd}$ component

| component | 10% | 15% | 20% | 25% | 30% |
|---|---|---|---|---|---|
| methyl | 20-23 | | 12-20[1] | | |
| ethyl | ca. 25 | | ca. 25 | | |
| propyl | 20-23 | 20-25 | 12-20[2] | 15-20 | 18-21 |
| methyl:propyl, 1:1 | | | ca. 32 | | |

[1] DSC showed that this sample crystallized at ca. −30° C. on cooling, then melted at 12-20° C. on rewarming. DSC also showed that a sample containing 13% methyl 4-hydroxybenzoate crystallized at ca. −25° C.
[2] DSC showed crystallization at ca. −25° C., Example 2

Preparation of an Aqueous Composition Comprising DCOIT/IPBC/methyl 4-hydroxybenzoate The ingredients listed below in Table 2 were combined according to the procedure stated below. DSC analysis of the resulting dispersion revealed a crystallization point on cooling of −30° C.

TABLE 2

| | Ingredient | Amount, % |
|---|---|---|
| 1 | water | 60.30 |
| 2 | DCOIT | 13.50 |
| 3 | IPBC | 6.50 |
| 4 | Branched $C_{11}$ alcohol, 7 units ethylene oxide | 1.50 |
| 5 | Branched $C_9$-$C_{11}$ alcohol, 2.5 units ethylene oxide | 1.50 |
| 6 | magnesium aluminum silicate | 0.30 |
| 7 | Xanthan Gum | 0.50 |
| 8 | copper EDTA | 0.90 |
| 9 | Kaolin FP 80 | 10.00 |
| 10 | Methyl 4-hydroxybenzoate | 5.00 |

Charged 20% instead of 60.3% of 1. Added 4 and 0.5% instead of 1.5% of 5. Mixed homogeneously under stirring. Added 10 and heated to 45-50° C. and added subsequently molten 2 under stirring and mixed homogeneously. Added the $2^{nd}$ portion of 1 (40.3%). Cooled down to 25° C. Added 3, 9 and 8 in series and mixed homogeneously by stirring. Added 6 in portions while stirring to homogeneity and added 7 that was wetted (pre-mixed) with the remainder of 5 (1%). Mixed homogeneously. The mixture was ground to 40μ by means of a DYNO Mill. The milling temperature was kept below 26° C. Appearance of final mixture: bluish-greenish dispersion, pH ~7.4

Example 3

Aqueous Composition with Varying Amounts of Methyl 4-hydroxybenzoate

Samples of the composition described in Example 2 were prepared with 0-5% methyl 4-hydroxybenzoate (HMB). A portion of the samples was heated to 40° C. for two hours, then cooled to room temperature (r.t.), while another portion was kept at room temperature throughout. Observations of the samples at various times are tabulated below in Table 3.

TABLE 3

| % HMB | pH | 2 h, 40° C. | 3 days, 40° C. -> r.t. | 2 h, r.t. | 3 days, r.t. |
|---|---|---|---|---|---|
| 0 | 6.92 | ffp[1] | ffp | ffp + aggl[2] | ffp + aggl |
| 1 | 6.92 | ffp | ffp | many aggl | many aggl |
| 2 | 6.87 | ffp | ffp | few aggl | few aggl |
| 3 | 6.85 | ffp | ffp | v. few aggl | v. few aggl |
| 4 | 6.87 | ffp | ffp | ffp | ffp |
| 5 | 6.84 | ffp | ffp | ffp | ffp |

[1]free-flowing paste
[2]agglomerates

The invention claimed is:

1. A biocidal composition comprising a mixture of:
   (a) from 50% to 70% 4,5-dichloro-2-octyl-3(2H)-isothiazolone;
   (b) from 20% to 30% 3-iodopropargyl-N-butyl carbamate; and
   (c) from 5% to 30% of at least one $C_1$-$C_4$ alkyl 4-hydroxybenzoate;
wherein percentages are based on total amount of components (a), (b) and (c).

2. The composition of claim 1 in which said at least one $C_1$-$C_4$ alkyl 4-hydroxybenzoate is at least one of methyl 4-hydroxybenzoate, ethyl 4-hydroxybenzoate and propyl 4-hydroxybenzoate.

3. The composition of claim 2 comprising from 52% to 68% of 4,5-dichloro-2-octyl-3(2H)-isothiazolone, from 20% to 28% 3-iodopropargyl-N-butyl carbamate and from 10% to 25% of at least one of methyl 4-hydroxybenzoate, ethyl 4-hydroxybenzoate and propyl 4-hydroxybenzoate.

4. The composition of claim 3 further comprising at least one surfactant.

5. The composition of claim 4 in which a mixture of 4,5-dichloro-2-octyl-3(2H)-isothiazolone, 3-iodopropargyl-N-butyl carbamate and at least one of methyl 4-hydroxybenzoate, ethyl 4-hydroxybenzoate and propyl 4-hydroxybenzoate comprises from 15% to 35% of the composition; water comprises from 50% to 75% of the composition; and a combination comprising surfactants, inorganic fillers and thickeners comprises from 10% to 20% of the composition.

6. The composition of claim 5 in which the surfactants comprise at least one $C_9$-$C_{11}$ branched alcohol ethoxylated with 2-10 moles of ethylene oxide and the inorganic fillers comprise kaolin.

7. A biocidal composition comprising:
   (a) from 10% to 18% 4,5-dichloro-2-octyl-3(2H)-isothiazolone;
   (b) from 4.5% to 9% 3-iodopropargyl-N-butyl carbamate;
   (c) from 2% to 8% of at least one $C_1$-$C_4$ alkyl 4-hydroxybenzoate;
   (d) from 50% to 72% water; and
   (e) from 10% to 20% of a combination comprising surfactants, inorganic fillers, and thickeners.

8. The biocidal composition of claim 7 in which said at least one $C_1$-$C_4$ alkyl 4-hydroxybenzoate is at least one of methyl 4-hydroxybenzoate, ethyl 4-hydroxybenzoate and propyl 4-hydroxybenzoate.

9. The biocidal composition of claim 8 in which the surfactants comprise at least one $C_9$-$C_{11}$ branched alcohol ethoxylated with 2-10 moles of ethylene oxide and the inorganic fillers comprise kaolin.

10. The biocidal composition of claim 9 comprising from 10% to 18% 4,5-dichloro-2-octyl-3(2H)-isothiazolone; from 4.5% to 9% 3-iodopropargyl-N-butyl carbamate; from 2% to 8% of at least one of methyl 4-hydroxybenzoate, ethyl 4-hydroxybenzoate and propyl 4-hydroxybenzoate; from 50% to 72% water; from 6.5% to 13.5% of at least one inorganic filler; from 0.4% to 1.2% of at least one thickener; from 0.3% to 1.8% of at least one copper salt; and from 1% to 5% of at least one surfactant.

* * * * *